Figure 1:
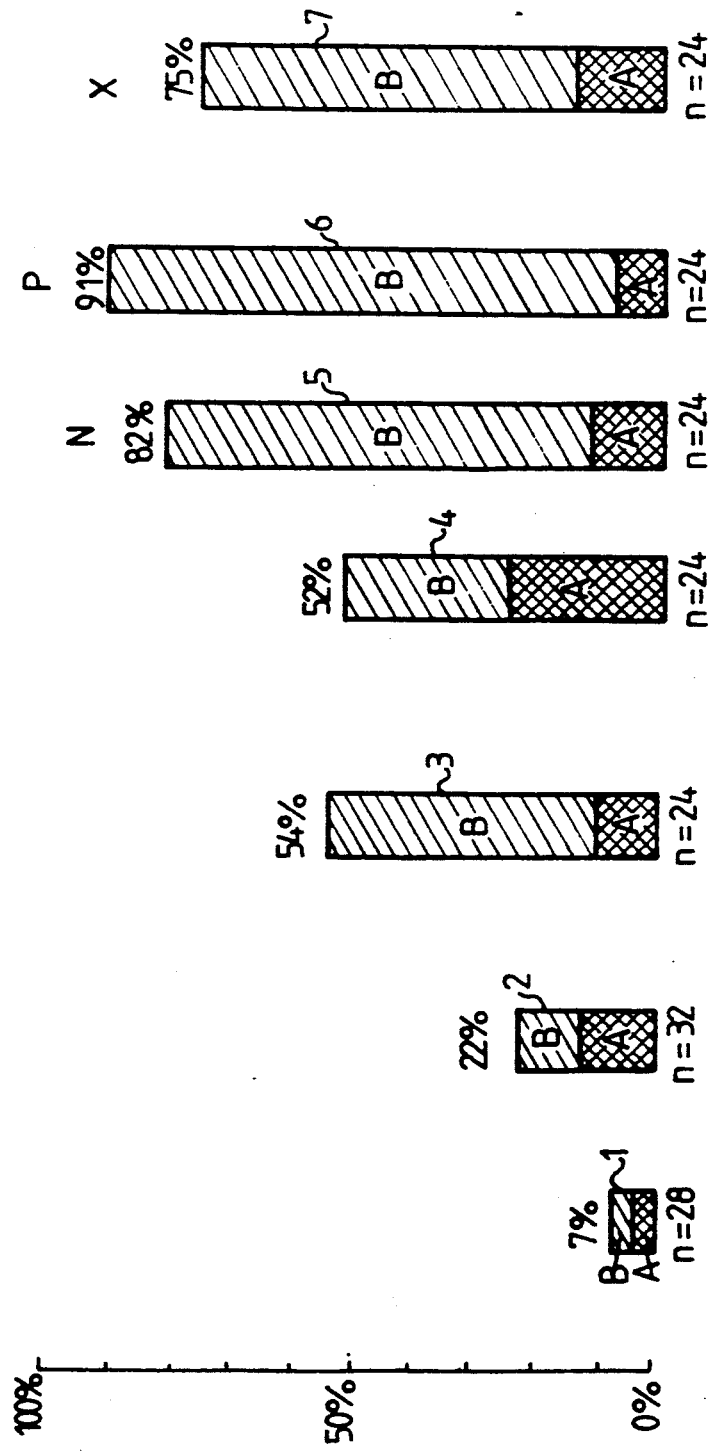

United States Patent [19]

Virag

[11] Patent Number: 5,145,852
[45] Date of Patent: Sep. 8, 1992

[54] VASO-ACTIVE MEDICAMENT TO TREAT IMPOTENCE

[76] Inventor: Ronald Virag, 5, avenue Clodoald, F-92210 Saint-Cloud, France

[21] Appl. No.: 550,779

[22] Filed: Jul. 10, 1990

[51] Int. Cl.⁵ ............... A01N 43/58; A01N 43/60; A01N 43/42; A01N 43/50
[52] U.S. Cl. ............... 514/253; 514/255; 514/256; 514/280; 514/307; 514/316; 514/386; 514/739; 514/929
[58] Field of Search ............... 514/307, 530, 280, 573, 514/253, 690, 248, 535, 542

[56] References Cited

U.S. PATENT DOCUMENTS 4,311,707  1/1982  Birnbaum et al. ............... 514/530
4,801,587  1/1989  Voss et al. ............... 514/248

FOREIGN PATENT DOCUMENTS 0346297  5/1989  Italy .

OTHER PUBLICATIONS

CA: 109(19)—163408 (Nov. 1988).

*Primary Examiner*—Leonard Schenkman
*Assistant Examiner*—T. J. Criares
*Attorney, Agent, or Firm*—Browdy and Neimark

[57] ABSTRACT

The invention pertains to the field of vasoactive medicines.

The vasoactive medicine, of the type composed of a combination of main active ingredients with papaverine, is characterized by the fact that it comprises at least one alpha blocker and a phosphodiasterase inhibitor representing a total of 5 to 20% by weight of the papaverine.

Application to treatment of impotence in men.

7 Claims, 1 Drawing Sheet

VASO-ACTIVE MEDICAMENT TO TREAT IMPOTENCE

This invention pertains to a vasoactive medicine that is applicable in particular to the treatment of impotence in men.

A considerable amount of research work in this field has made it possible, first of all, to identify the mechanism and the various phases of erection, then to define the necessary properties, particularly vasoactive, of active and tolerable products. In particular, multiple clinical studies have made it possible to select papaverine and to clarify how it works, then to combine it with alpha blocking products such as phenoxybenzamine and phentolamine (BRINDLEY GS—Cavernosal Alpha-blocate, a new techni[que] for investigating and treating impotence—BRIT. J. P[S]YCHIATRY 143, 1983). Prior work by the applicant has also made possible the detailed study of isolated and/or potentiating activity of numerous vasoactive substances (cf. "Papavérine et Impuissance: la voie pharmacologique" [Paperavine and Impotence: the pharmacological way] Ronald Virag, EDITIONS DU CERI, Paris, 1987) primarily the combination of the two above alpha blockers and papaverine.

The clinical use of the discovery has developed at the same time, with the use of two methods, i.e., perfusion and self-injections by the patient immediately before the sexual act (see the above-cited work).

However, the study of the initial results observed leads to two findings:

1. That no more than 50% of all impotent patients could be treated with papaverine alone, with the combination of papaverine and alpha blocker or with prostaglandin alone (PGE1);

2. Regardless of the product, in 10 to 30% of the erections produced, there is a risk of blocking of the erection, which varies depending on the drug used, the dose injected and the etiology of the impotence, with the risk that this prolonged erection will lead to a real priapism.

Considering the data collected through experimental studies and clinical results, the ideal product to be injected would be able to trigger a complete erection in 100% of the patients with no risk of blocked erection, and with no general clinical effects: it was found that none of the products used or tested to date corresponds to such a description.

Considering the local conditions under which the erection occurs, the applicant indeed determined that, to have this maximum effectiveness, the ideal product should be active in the different phases of the erectile cycle, and consequently that such effectiveness could only be achieved in the current state of available products through a combination of several main active ingredients, with the specific effects of each product making it possible to extend and reinforce the effects of the others.

In accordance with the invention, the vasoactive medicine is primarily composed of papaverine, in combination with main active ingredients containing at least one alpha blocker and one phosphodiasterase inhibitor, as well as, advantageously, a PGE1-type prostaglandin, a dopaminergic agent and an atropinic agent, with the alpha blocker itself being composed of one part $alpha_1$ and one part $alpha_2$, these ingredients representing a total of 5 to 20% by weight of the papaverine in an injectable aqueous solution.

FIG. 1, the sole FIGURE, is a graph showing the results of clinical tests set forth in Example 2, below.

It is known that papaverine acts as a myorelaxer of the smooth musculature through direct action on cyclical AMP. whose inactivation it prevents. Secondary pharmacological actions were noted but were not demonstrated in the erectile tissue: discrete alpha blocking action[,] positive ganglioplegic action.

$Alpha_1$ blockers act by inhibiting alpha-adrenergic transmission at the post-synaptic level;

$Alpha_2$ blockers act by inhibiting this transmission at the presynaptic level;

The local mechanism that controls the action of dopamine or dopaminergic drugs on the erectile tissue has not to date been clarified, but the applicant found clinically that the product acts positively on erections;

Atropine has no effects on healthy erectile tissue. The product works by potentiating the action of the other active products on pathological erectile tissue by interfering with the mechanisms that trigger the relaxation of smooth muscle, especially the EDRF (Endothelium Releasing Factor);

Phosphodiasterase (dipyridamol type) inhibitors work by prolonging the action of the other products as well as through their anti platelet aggregation action. Locally, they prevent the risk of intracavernous blood thrombosis when the erection is prolonged;

Prostaglandin $PGE_1$, or a similar material, acts as a relaxant for the smooth musculature at an earlier stage than the papaverine, whose action it completes, the two products potentiating each other.

Consequently, each of the active products in the medicine according to the invention not only has its expected effects on a given stage of the erection mechanism, but, furthermore, due to this effect itself, it prepares and facilitates, even accentuates, the effects of the other active products, while inhibiting harmful side effects.

The following examples, provided solely on an illustrative and non-restrictive basis, demonstrate the above-mentioned effects and provide a clearer understanding of the advantage and scope of the invention.

EXAMPLE 1

Compounds

The clinical studies described below were conducted based on the following three compounds, in comparison with known products.

a) Compound N, comprising the following per 1 ml of injectable solution:
papaverine 20 mg
ifenprodil tartrate 0.75 mg ($alpha_1$ blocker)
atropine 0.025 mg (anticholinergic)
yohimbine 0.075 mg ($alpha_2$ blocker)
dipyridamol 0.25 mg (phosphodiasterase inhibitor)
piribedil 0.225 mg (dopaminergic)

b) Compound P comprising, in addition to the derivatives mentioned above for compound N, 33 µg of alprostil (Prostaglandin $PGE_1$) per ml of injectable solution;

c) Compound X containing the following per 1 ml of injectable solution:
papaverine 20 mg
phentolamine 1 mg (alpha blocker)
PGE1 33 µg (prostaglandin)

dipyridamol 0.25 mg (phosphodiasterase inhibitor)

EXAMPLE 2

Clinical Tests

The study to test the different products among themselves was conducted by injecting 0.2 ml of the product tested per 100 ml of flaccid penis, a volume calculated in a manner known in and of itself (cf. the above-cited work). Ten minutes after this injection, patients were exposed to visual sexual stimulation (VSS) for 10 minutes.

Each product was tested by series randomization of 23 to 30 patients.

The volume of the penis was measured every three minutes using a chart; rigidity was measured using a specialized device known as a rigidimeter, calibrated at 0 to 200 PR (Penrig) units, in which the most important values are as follows:

- up to 35 PR: no signification variation;
- 35 to 50 PR: significant tumescence with considerable change in volume;
- 55 to 75 PR: beginning of rigidity;
- 75 PR and above: limit of rigidity needed for penetration;
- 100 PR and above: normal rigidity corresponding to complete venous blockage.

The percentage of patients in whom a complete erection (rigidity of over 75 PR) was produced for more than half of the visual stimulation time and which lasted at least one minute after this stimulation ended is used as a comparative measurement.

The results of this study are illustrated in the accompanying synoptic graph which for each product shows blocks whose height is measured according to a graduated scale of 0 to 100% of total erection. Each block also shows the percentage of non-lasting complete erection after VSS (A) and lasting at least one minute after VSS (B), as well as the number n of subjects who underwent the test. All of the measurements were taken after a local intra-cavernous injection of 0.2 ml of product, namely: a control or placebo of physiological serum (1), 40 mg/ml of papaverine (2), 40 mg of papaverine combined with 0.5 mg of phentolamine per ml (3), 33 $\mu$g/ml of PGE$_1$ (4), and compounds N (5), P (6) and X (7) according to the invention.

In reference to this graph, the results demonstrate that the three compounds N, X and P respectively produced 82, 75 and 91% complete erections according to the identified criteria. Conversely, the placebo, papaverine, prostaglandin alone and the combination of papaverine and phentolamine respectively produced 7, 22, 52 and 54% complete erections. It can be noted that the compounds according to the invention yielded these results with half the content of papaverine.

Another factor that must be considered is the capacity of a product to trigger a prolonged erection, which is a risk when it lasts longer than three hours. The presence of atropine and the phosphodiasterase inhibitor allows the blocking power of compounds N and P to be lower than that of the other combinations most effective in this respect, namely, papaverine, phentolamine, which is an additional advantage over products already used in this field.

EXAMPLE 3

Clinical Studies

A total of 264 impotent patients underwent self-injection treatment with the compounds according to the invention.

After preliminary tests, one or two intracavernous injections were performed per week, prior to the sexual act. 221 of these patients (4.12%) [sic]suffered from organic impotence; 136 (51.51%) would have been advised to have surgery without the medication; 64 (24%) were recommended for penile prosthesis implants.

Among the 230 patients regularly studied: 19 were classified as obtaining poor results, 5 were unclassifiable due to insufficient use of the method, 12 yielded average results (sex life resumed in a satisfactory manner), 176 were considered good and 17 as very good. For 205 of these 230 patients (i.e., 89.13%) normal sexual activities were resumed. In 8.69% of the patients, recovery was complete, treatment was discontinued; for 12.6% injections were not used in over 50% of the sexual acts; and finally, in 42.6% of the cases, the patient was entirely dependent on the treatment. These results were obtained with no general or local complications outside of 5.8% hematomas at the point of injection, considering that, unlike other injected products, a compound according to the invention is completely painless when entering the cavernous body.

Of course, this invention was described and represented only on an explanatory and non-restrictive basis, and any useful modification, primarily in the area of technical equivalencies, may be made without departing from its scope.

What is claimed is:

1. A pharmaceutical composition applicable to the treatment of impotence in men, composed of a combination of main active ingredients with papaverine, wherein said main active ingredients comprise
    an alpha blocker selected from the group consisting of phentolamine, ifenprodil, yohimbine and mixtures thereof; dipyridamol as a phosphodiasterase inhibitor; atropine as an anticholinergic; and
    piribedil as a dopaminergic, or a prostaglandin selected from the group consisting of PGE$_1$ and alprostil, or both said piribedil and said prostaglandin,
    all of said main active ingredients representing a total of 5 to 20% by weight of the papaverine.

2. A composition according to claim 1, having per 1 ml of injectable solution: papaverine 20 mg; infenprodyl tartrate 0.75 mg as an alpha$_1$_ blocker; yohimbine 0.075 mg as an alpha$_2$_ blocker; atropine 0.025 mg as said anticholinergic; piribedil 0.225 mg as said dopaminergic.

3. A composition according to claim 1 having per 1 ml of injectable solution: papaverine 20 mg; ifenprodil tartrate 0.75 mg as an alpha$_1$_ blocker; yohimbine 0.075 mg as an alpha$_2$_ blocker; atropine 0.025 mg as anticholinergic; piribedil 0.225 mg as said dopaminergic; alprostil 33 $\mu$g as said prostaglandin.

4. A composition according to claim 1, having per 1 ml of injectable solution: papaverine 20 mg; phentolamine 1 mg as said alpha blocker; dipyridamol 0.25 mg as said phosphodiesterase inhibitor; alprostil 33 $\mu$g as said prostaglandin.

5. A composition according to claim 1, wherein said alpha-blocker is a mixture of ifenprodil tartrate and yohimbine.

6. A composition according to claim 1, comprising papaverine, dipyridamol atropine, ifenprodil tartrate, yohimbine and piribedil.

7. In a pharmaceutical composition having a vasoactive effect applicable to the treatment of impotence in men, composed of a combination of main active ingredients with papaverine, the improvement consisting of:

an injectable solution having a composition for 1 ml of said solution of papaverine approximately 20 mg; ifenprodil tartrate approximately 0.75 mg as an alpha$_1$ blocker; atropine approximately 0.025 mg as an anticholinergic; yohimbine approximately 0.075 mg as an alpha$_2$ blocker; dipyridamol approximately 0.25 mg as a phosphodiasterase inhibitor; piribedil approximately 0.225 mg as a dopaminergic; and alprostil approximately 33 μg as a prostaglandin.

* * * * *